United States Patent [19]

Dupain

[11] 4,391,774
[45] Jul. 5, 1983

[54] AUTOMATIC DEVICE FOR MAKING SAMPLES FOR ANALYSIS

[75] Inventor: Jean Dupain, Saint Maur, France

[73] Assignee: Societe des Ciments Francais, Guerville, France

[21] Appl. No.: 273,751

[22] Filed: Jun. 15, 1981

[30] Foreign Application Priority Data

Jun. 27, 1980 [FR] France .................. 80 14302

[51] Int. Cl.³ ........................................ G01N 35/00
[52] U.S. Cl. ............................ 422/63; 141/83; 141/103; 177/50; 177/52; 414/21; 414/186; 422/67; 422/68; 422/50; 436/174
[58] Field of Search ........................ 422/63–68, 422/50; 414/21, 180, 186; 141/83, 103; 177/50, 52, 55, 150, 54

[56] References Cited

U.S. PATENT DOCUMENTS

| | | | |
|---|---|---|---|
| 2,741,374 | 4/1956 | Morgan ................ | 414/186 X |
| 3,870,465 | 3/1975 | Marechal .............. | 422/68 X |
| 4,058,367 | 11/1977 | Gilford .................. | 422/67 X |
| 4,113,436 | 9/1978 | Werder et al. ........ | 422/65 |
| 4,248,315 | 2/1981 | Falinower ............. | 177/145 X |

*Primary Examiner*—Michael S. Marcus
*Attorney, Agent, or Firm*—Darby & Darby

[57] ABSTRACT

A device is disclosed for continuously making samples to be analyzed by known instruments such as an X-ray spectrometer. The device consists of means for depositing a crude composition and associated vitrifying agent together in a crucible in accordance with a predetermined ratio by weight. The crucible is heated to melt its contents into an homogenous liquid mixture which is cooled to form a solid beadlet to be analyzed. The beadlet is conveyed to the analyzing instrument. A computer measures the respective weights of the components of the crucible contained composition and non-conforming weight measurements result in the crucible being discarded and replaced by another.

21 Claims, 5 Drawing Figures

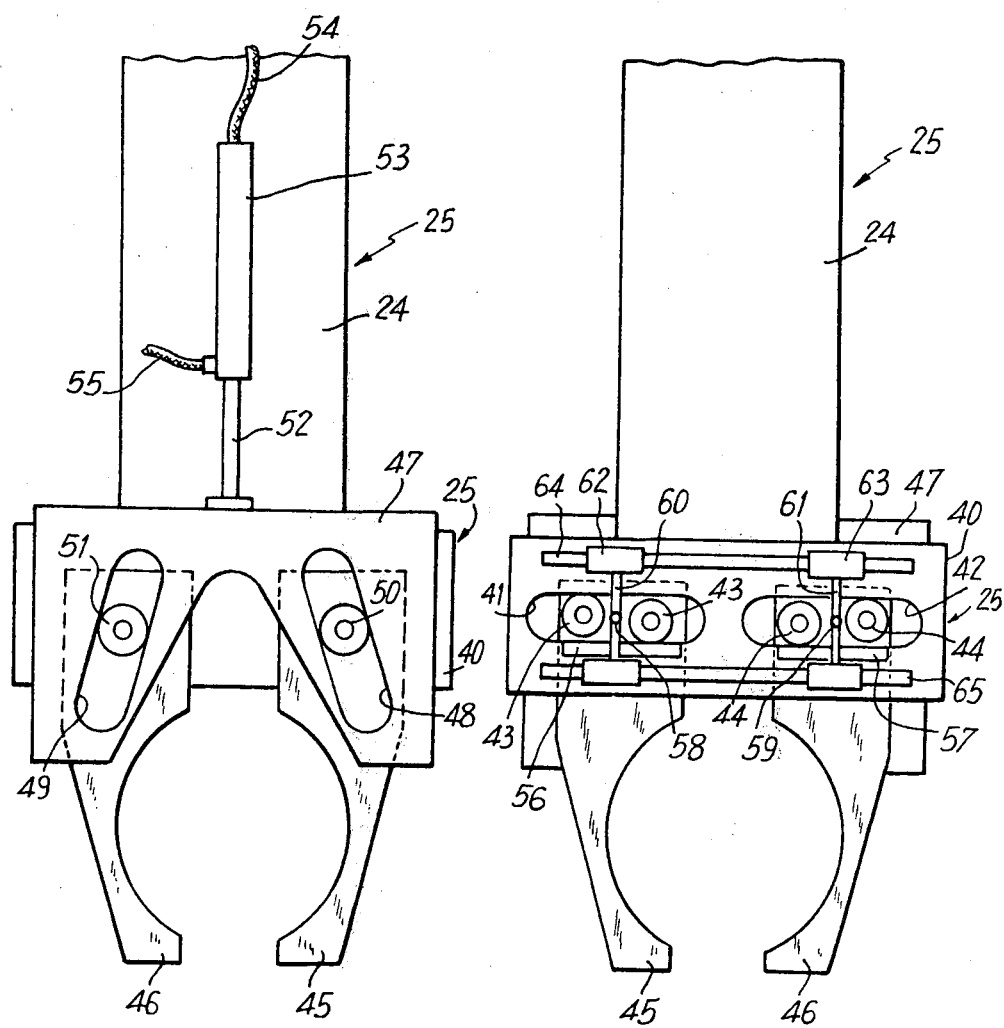

AUTOMATIC DEVICE FOR MAKING SAMPLES FOR ANALYSIS

OBJECTS AND SUMMARY OF THE INVENTION

The object of the present invention is a device for automatically making samples adapted for being analyzed so as to determine the exact composition of the constituent elements of the samples, said samples being made of a mixture provided with a dosage accurate to the milligram of flux and analysis powder, said mixture being adapted to be melted and cooled so as to obtain a beadlet which is introduced in the analysis apparatus.

This device is particularly provided for cement factories for the analysis of the composition of mixtures of components after they have been crushed and before they are burnt in a furnace, oven, said products being usually called "crudes". Said crudes are constituted by quarry products and the proportion of the various components (clay, silica, etc.) has to be constant in order that the final product, called "clinker", obtained after the burning, has a well determined and constant quality.

In order to obtain such a regularity in the composition of the crudes, analyses are regularly carried out, generally by using X rays spectrometers, which require that the samples be of a very fine granules and have a perfectly plane surface.

According to a first method, a determined volume of crude powder is crushed into particles of the order of a few microns, by a ring crusher after having been transformed into paste by addition of alcohol, the alcohol being then evaporated for providing a crusty product which is reduced into powder and compressed at a very high pressure, thereby giving a pellet, kept in a metallic ring or a capsule, said wafer being introduced in the X ray spectrometer. Thus can be obtained a measurement about every 15 minutes, which allows controlling the units feeding the crude silos. However, such measurements are not accurate enough and may be erroneous since the silica grains break up differently according to their mineral composition, thereby altering the X ray measurement, and it happens on the other hand that the surface state of the wafer is not perfectly plane, this altering also the measurement.

According to a second method, the sample to be analysed is vitrified, meaning that crude powder and a flux mixture is prepared in a proportion which is very accurately determined, and this mixture is melted at a high temperature (about 1200° C.) so as to obtain a homogeneous glass from the two products. After cooling, a beadlet is obtained having the appearance of a more or less tinted glass. The beadlet is then introduced in the X ray spectrometer.

The measurements thus obtained are much more reliable. The making of the beadlets requires however a very meticulous handling when weighing the two components, the weighing having to be very accurate, since the precision of the measurement is a function of the ratio of the quantities of the two glass components, and for the subsequent burning and analysis operations, so that these analyses cannot be carried out continuously and at a cadence sufficient for permitting piloting and regulating the feeding installations of the crude product silos.

The object of the present invention is a device providing the automatic formation of the beadlets and their introduction into an X ray spectrometer.

BRIEF DESCRIPTION OF THE DRAWINGS

By way of a non limiting example and in order to facilitate the description of the invention, reference is made to the accompanying drawings wherein:

FIG. 2 is a detailed plan view at a larger scale showing the pliers of the rotatable arm of the installation shown in FIG. 1, FIG. 3 is a view from below of the pliers of FIG. 2.

DETAILED DESCRIPTION OF THE EMBODIMENT

Figure 1:
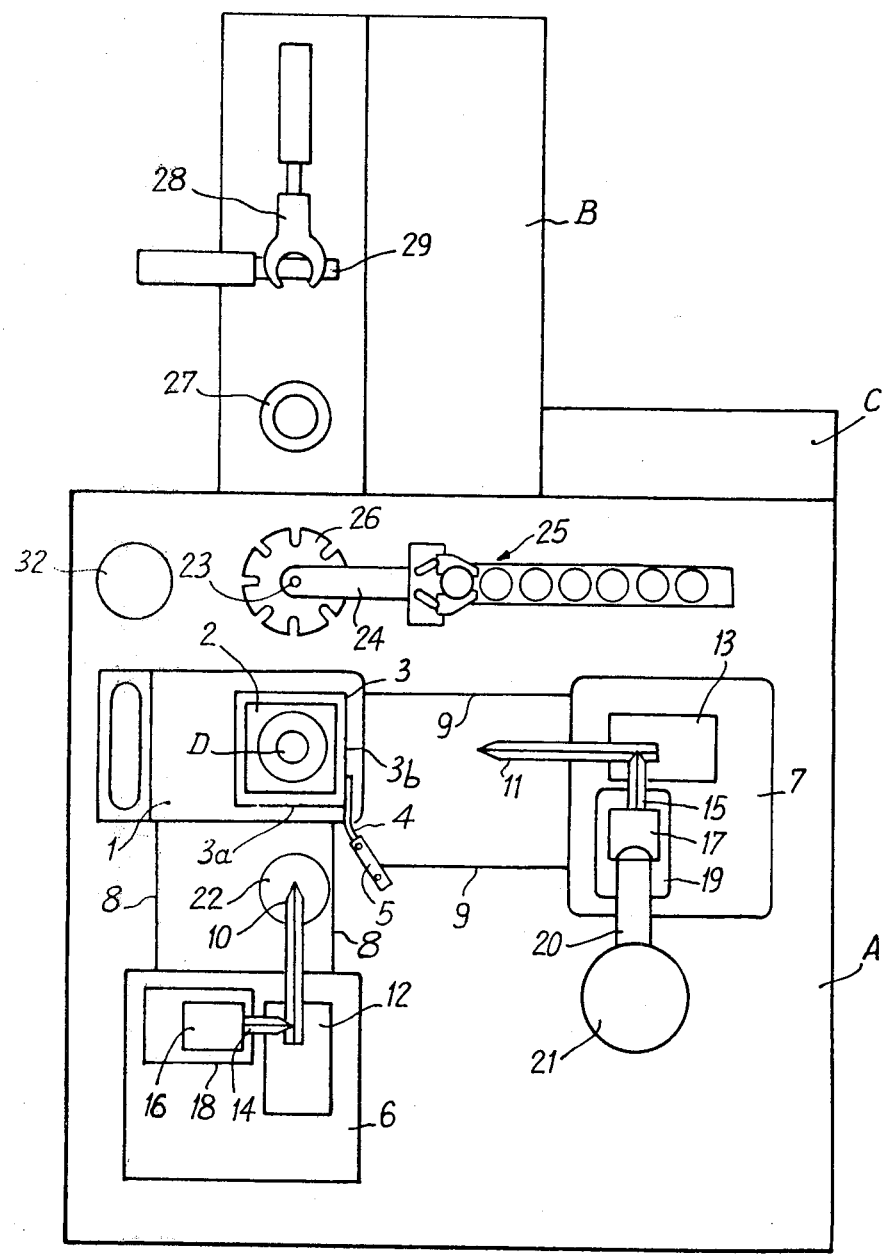
FIG. 1 is a schematic plan view of an installation for making the beadlets.

Reference being made to FIG. 1, one sees that the device comprises a balance or scale 1, placed on an anti-vibration assembly independent of plate A, which is preferably an elecronic scale with a precision of the order of a milligram. The plate 2 of the scale is preferably covered with a bell 3, which, in the example shown, is a glass cube formed with a window 3a on one side face and a window 3b on another face. Said bell 3 is carried by an arm 4 connected to a frame 5, carried by a jack, not shown.

The plate A also carries two carriers 6 and 7, mobile on rails 8 and 9. Each carrier is provided with a spout 10 and 11, mounted on a vibrating stand 12 and 13 and a second gutter 14 and 15 fed from a hopper 16 and 17, the whole being mounted on a vibrating stand 18 and 19. In addition, the hopper 17 is fed via a gutter 20 connected to a tank 21 of great volume.

Each carrier is moved by an electric motor, not shown, the operation of which is controlled, in known manner, by end of stroke micro-switches so as to occupy either a waiting position which is that shown in FIG. 1, or an advanced position in the immediate vicinity of scale 1. When the carrier 6 or 7 is in the advanced position, the ends of spouts 10 and 11 are in vertical alignment with the center of plate 2 of the scale after having penetrated inside bell 3 through one or the other of windows 3a or 3b. When the carrier 6 is in the waiting position shown in FIG. 1, the end of the spout 10 is in vertical alignment with a discharge opening 22.

The hopper 16 receives the product to be analysed, while the hopper 17 receives the flux.

The plate A carries, on the other side of scale 1, a vertical rod 23, carried by a piston not shown, so as to be capable on the one hand to rotate about its own axis, and on the other hand to slide longitudinally. Said rod 23 carries an arm 24 provided at its end with pliers 25. The pivoting movement of rod 23 and of arm 24 is controlled, in a manner known per se, by a mechanism cooperating with a disc 26 provided, in the example shown, with 8 notches angularly spaced at 45° from each other.

On the side of plate A is disposed the induction furnace B, also known as such. This burning furnace comprises a piston 27, adapted for receiving a crucible D handled by the pliers 25, said piston, once provided with its crucible, presenting said crucible inside a winding which heats the crucible by induction; after fusion, the crucible is handled by the pliers 28 which pour the content of the crucible into a cupel where the melted liquid cools down by forming the beadlet which is discharged on a chute 29.

A programmer C controls the sequential progress of the various operations hereafter described.

The hopper 16 is supplied by any appropriate known means, for example by a pneumatic transport of the product to be analysed, namely a sample from the receiving station of the crude material storage silo. The hopper 16 contains approximately 40 g of sample. This product has to be mixed to the flux in a determined proportion.

During a first period, the pliers 25 are in the starting position above the end of a ramp loaded with a row of crucibles. It is set in action by the programmer C in order to pick up a crucible D and to pivot it for bringing it above the plate 2 of scale 1, the bell 3 having been lifted out of the way of the arm 24 and the pliers 25.

Then, the vibrating stands 12 and 18 are set in action by the programmer C while the carrier 6 is in a waiting position: the result is that the product flows from the hopper 16 via the chute 14 and from there into chute 10, from where it falls through the discharge hole 22: the vibrating stands 12 and 18 are interrupted at the end of a determined period corresponding to the flow of about half the content of hopper 16, viz. approximately 20 grams. The object of this operational phase is to eliminate any quantity of powder remaining from the previous sampling.

The carrier 6 is then set in action, so that it moves towards scale 1, its chute 10 penetrates into the bell 3 via window 3a and the carrier 6 stops at the end of its stroke, the end of the chute 10 being in vertical alignment with a crucible D placed on the scale plate. The vibrating stands 12 and 18 are then set again in action and the powder flows into the crucible D.

The scale records the weight increase and transmits continuously to the programmer C the data of the weighing. As soon as 2.5 g of powder, in the present example, have fallen into the beaker, the programmer C stops the vibrating stands 12 and 18. The exact weighings, to the nearest milligram is then recorded by the programmer C which comprises a device of the minicomputer type, which can store the data and carry out simple arithmetic operations. The value of the weighing is stored. If the value is more than 2.7 g, the quantity of flux to be added thereafter would be too important and the operation is cancelled and started again. For so doing, the carrier 6 moves back, the frame jack lifts frame 5, which in turn lifts the bell 3, the arm 24 pivots, moves down, picks up crucible D, pivots about 90° and releases crucible D which falls in the discharge opening 32. If the weighing value is less than 2.700 g, for example 2.506, this data is stored and multiplied by 4, in our example, namely 10.024. The carrier 6 moves back to its waiting position.

The carrier 7 is then set in action and moves forward toward scale 1, its spout 11 penetrates into bell 3 through window 3b, and when its stops at the end of its stroke, the end of said spout 11 is in vertical alignment with crucible D. The vibrating stands 13 and 19 are then set in action and the vitrifying product is poured out. The scale records the weight increase and stops the flow as soon as the value previously calculated, viz. 10.024 in the example in consideration is reached. The weighing is then carried out, with an error of 3 mg being admitted since this corresponds to a weighing error on the product to be sampled which is less than a milligramme. If at the time where the apparatus stops the product tumbles slightly and causes an error which is more than 3 mg, the programmer cancels the operation, meaning that the pliers 25 pick up the crucible D as previously and release it into the opening 32.

The fluidity of the flux being generally superior to that of the crude sample, the risks of error are smaller for the weighing of the flux than for the weighing of the crude material sample and, on the other hand, the ratio of these materials being, in our example of 1:4, the incidence of an error on the flux is less important.

If the weighing is correct, the carrier 7 moves back to its starting position. The bell 3 is then lifted by the frame 5 and the pliers 25 pick up the beaker. For so doing, the rod 23 slides longitudinally upwardly, thereby lifting the arm 24 and the pliers 25, then, by being guided stepwise by the disc 26 formed with notches (also called Maltese cross control member), the rod 23, the arm 24 and the pliers 25 pivot so as to bring the pliers exactly above crucible D. The rod 23, and therefore the arm 24 and the pliers 25, move down, and the arms of the pliers pick up crucible D. The rod 23, arm 24 and pliers 25 assembly moves again upward and pivots about 180° in order to come above piston 27, where it moves down in order to place the crucible on a ceramic stud provided at the end of the rod of piston 27.

The induction furnace B operates in known manner, meaning that the piston 27 lifts the crucible D for bringing it inside the windings of the induction heating coil; the powder mixture is set in fusion, then the heating is interrupted several times for obtaining a better homogenization of the melted product; the pliers 28 pick up the beaker and the ceramic stud and pours the product in fusion in a platinum cupel where it solidifies by forming what is called a beadlet. The beadlet is then taken from the mold and falls on an inclined plane 29.

Figure 4:
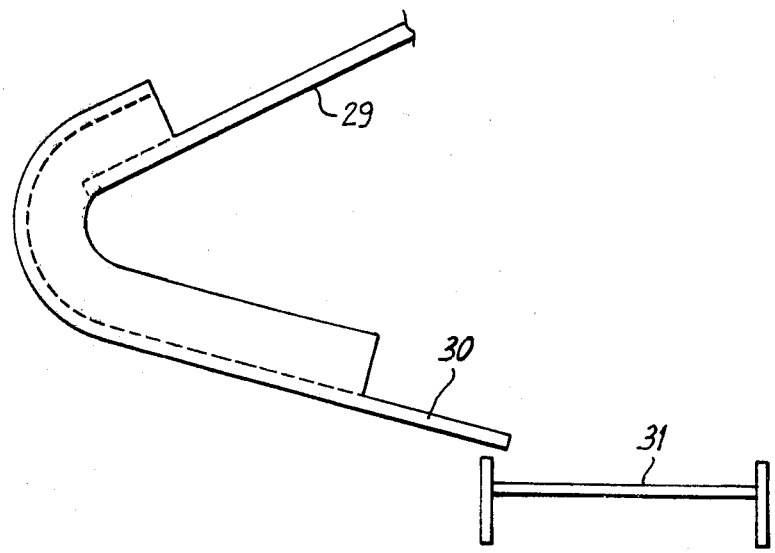
FIG. 4 is a detailed view at a larger scale of the reversing chute of the device of FIG. 1.

The inclined plane 29 causes the beadlet to slide to inside the curve of a chute 30 (FIG. 4), the effect of which is to turn the beadlet over so as to put it in the correct position; said chute places the beadlet on a conveyor-belt 31. The draining operation of the product hopper 16 is then started by setting the vibrating stands 12 and 18 in vibration. According to the process of the mill, this operation can be retarded for the eventual making of a second beadlet from the same sample.

Figure 5:
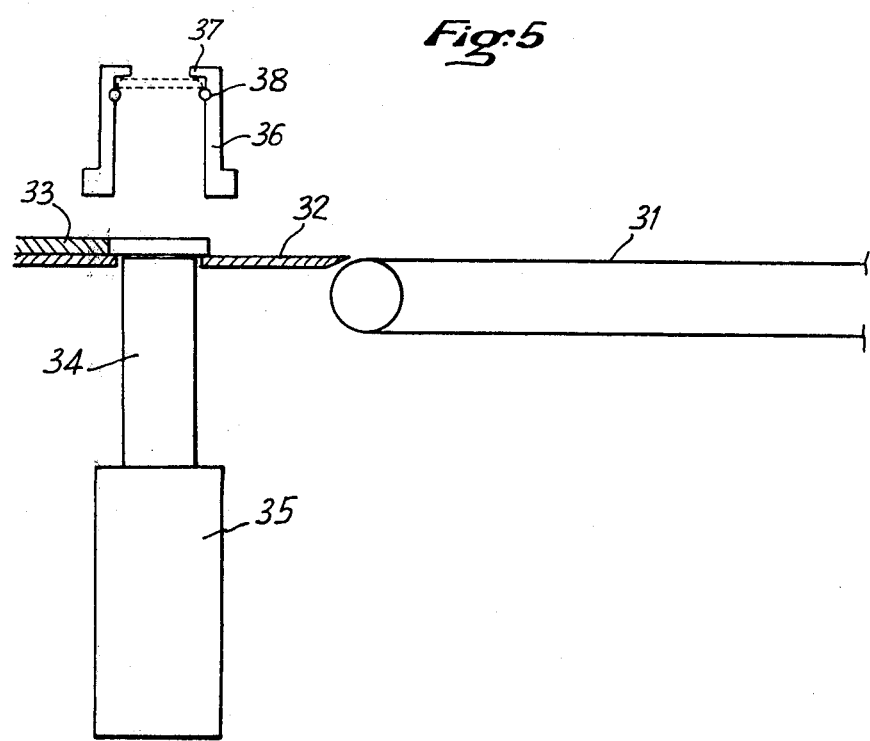
FIG. 5 is a detailed view illustrating the loading device of the beadlets in the sample holder.

At its end, the conveyor 31 unloads the beadlet on a plaquette 32 (FIG. 5), the end of which comprises a rounded abutment 33 having practically the same size as the beadlet so as to position it with precision relative to an end of the rod 34 of a piston 35. The rod 34 of piston 35 lifts the beadlet and brings it inside the sample-holder 36 by pushing it against the edge 37 of the sample-holder where it is blocked by the ball clipping arrangement 38.

FIGS. 2 and 3 show a preferential embodiment of the pliers 25. Referring to said Figures, one sees that at the end of arm 24 is mounted a plate 40 formed with two oblong openings 41 and 42 in alignment.

In these two openings slide pairs of rollers 43 and 44 carried by two clutches 45 and 46, so that said clutches can move in translation away from each other or close to each other. A mobile plate 47 is placed on the other side of the clutches 45 and 46, which are thus maintained between the plate 40 and the plate 47. This plate is formed with two converging oblong openings 48 and 49 in which slide rollers 50 and 51 also carried by clutches 45 and 46. The plate 47 is connected to the rod 52 of a piston 53 which can be a pneumatic piston supplied by lines 54 and 55. One sees that by acting on the supply of jack 53, a displacement of plate 47 is caused in the longitudinal direction, thereby causing the lateral displacement of clutches 45 and 46.

Preferably, in order to have the clutches 45 and 46 well guided, two small slides 56 and 57 are placed along one of the sides of openings 41 and 42 and each roller 43 or 44 is made of two superimposed rollers, one of the couples of rollers 43 (44) bearing against one of the sides of opening 41 (or 42), the other bearing at the same time against the other side of the opening and against the slide.

Moreover, each clutch 45 (or 46) comprises a dog (58 (or 59) carrying a slightly flexible pin 60 (or 61) carrying at both ends rollers 62 (or 63) rolling on rails 64 (or 65) placed on the lower face of plate 40. This arrangement maintains the plate 40 and the clutches 45 and 46 assembled, with some elasticity.

This invention is not limited to the particular case described where the beadlet is meant to be introduced in an X ray fluorescent spectrometer. Indeed, instead of cooling the melted glass on platinum cupel, one can pour the melted material into a beaker filled with acid, the dissolution being then rapid and the solution obtained being directly analysed by atomic absorbtion for example, or by a plasma torch analysor.

On the other hand, in the example described, the ratio of the product to be analysed to the flux is of ¼, but it is obvious that it can be anything in the form of 1/n.

I claim:

1. A device for making samples for analysis, comprising:
   a furnace,
   a weighing station,
   a plurality of crucibles,
   a pair of carriers movable between first and second positions, each of said carriers having means for successively charging one of said crucibles at said station with one of two components of the sample when the carrier is in one of said positions,
   means for discarding said one crucible when the weight of one of the components therein differs from a predetermined amount,
   means for moving successive ones of a plurality of said crucibles to said station to be charged and to said furnace to melt the contents of the crucible,
   a mold adapted to receive the melted contents of the crucible to form the sample,
   means for transferring said melted contents to said mold and thereafter discarding the empty crucible, and
   control means for activating the means for charging, weighing, emptying and discarding of said crucibles.

2. The device of claim 1 in which one of said two components is a vitrifying agent.

3. The device of claim 1 in which said means for charging one of said crucibles comprises a hopper and at least one discharge spout.

4. A device according to claim 3, comprising means defining a discharge opening and wherein the discharge spout of one of said carriers is in vertical alignment with said discharge opening when said one carrier is in its first position.

5. A device according to claim 4 wherein the end of each of said discharge spouts is in vertical alignment with said weighing station when one or the other of said carriers is in its second position.

6. A device according to claim 5, comprising a bell cover removably supported by said weighing station and having a plurality of windows for letting through the spouts.

7. A device according to claim 6 comprising an antivibration stand supporting said weighing station and said moving means comprising a transfer arm provided with pliers for gripping the crucible, said arm being mounted for rotation about a vertical axis and for moving up or down to move the crucible to and from the scale.

8. The device of claim 7 comprising means for selectively vibrating each of said carriers.

9. A device according to claim 8, wherein said vibrating means vibrates said one carrier when said one carrier is in its first position during a predetermined period corresponding to the outflow through the discharge opening of substantially half the content of its hopper.

10. A device according to claim 9, wherein said vibrating means vibrates said one carrier when said one carrier is in its second position to cause the hopper to discharge one of said components into the crucible until a first predetermined weight is reached.

11. The device of claim 10 comprising means for moving the other of said carriers to its second position when said first weight is reached, said vibrating means being actuatable to cause the hopper of the other of said carriers to discharge the other of said components into the crucible until a second predetermined weight is reached.

12. The device of claim 11 comprising means for actuating said transfer arm to remove the crucible from the weighing station if said first predetermined weight is exceeded.

13. The device of claim 12 in which said actuating means actuates said transfer arm to remove the crucible from the weighing station if said second predetermined weight is exceeded.

14. A device according to claim 11, wherein the second predetermined weight is a predetermined multiple of the value of the first weight.

15. The device of claim 7 in which said pliers comprise a pair of clutches slidably mounted between two spaced apart plates, one of said plates being rigidly mounted on said transfer arm and having a pair of guiding slots, the other of said plates being movable and having a pair of converging slots, said clutches engaging said converging slots so as to be moved toward and away from each other during sliding movement between said plates.

16. The device of claim 15 comprising means for causing sliding movement of said clutches between said plates.

17. The device of claim 16 in which said causing means comprises a jack.

18. A device according to claim 7, comprising means for holding said plurality of said crucibles and wherein the arm can occupy four positions: a starting position in which the pliers are in vertical alignment with said holding means; a loading position in which the pliers are in vertical alignment with the weighing station; an unloading position in which the pliers are in vertical alignment with the furnace; and a discharge position in which the pliers are at 180° relative to their starting position.

19. The device of claim 7 comprising means for moving said transfer arm longitudinally in the direction of said crucibles.

20. A device according to claim 1 comprising an inclined plane connected to one end of a chute forming a reverse loop, a conveyor-belt below the other end of said chute, and means for removing said sample from said mold and placing said sample on the inclined plane from which it is deposited on the conveyor belt.

21. The device of claim 20 comprising:

a plane surface to receive the sample from the conveyor belt;

a jack to move the sample;

a rounded abutment on said plane surface to position the sample on the jack;

a sample holder having a cylindrical bore to receive the sample from said jack; and clip means connected to the holder to secure the sample within the holder.

* * * * *